United States Patent
Taskin et al.

(10) Patent No.: US 10,765,788 B2
(45) Date of Patent: Sep. 8, 2020

(54) AXIAL FLOW ROTOR WITH DOWNSTREAM BEARING WASH FLOW

(71) Applicant: HeartWare, Inc., Miami Lakes, FL (US)

(72) Inventors: Mustafa Ertan Taskin, Cooper City, FL (US); Ellen Keysselitz, Aachen (DE); Wolfgang Kerkhoffs, Aachen (DE)

(73) Assignee: Heartware, Inc., Miami Lakes, FL (US)

( * ) Notice: Subject to any disclaimer, the term of this patent is extended or adjusted under 35 U.S.C. 154(b) by 179 days.

(21) Appl. No.: 16/124,277

(22) Filed: Sep. 7, 2018

(65) Prior Publication Data
US 2019/0001034 A1    Jan. 3, 2019

Related U.S. Application Data

(63) Continuation of application No. 15/639,131, filed on Jun. 30, 2017, now Pat. No. 10,080,826, which is a
(Continued)

(51) Int. Cl.
*A61M 1/10*    (2006.01)
*A61M 1/12*    (2006.01)

(52) U.S. Cl.
CPC .......... *A61M 1/1017* (2014.02); *A61M 1/101* (2013.01); *A61M 1/1012* (2014.02);
(Continued)

(58) Field of Classification Search
CPC .............. A61M 1/1017; A61M 1/1012; A61M 1/1013; A61M 1/1029; A61M 1/122; A61M 1/101
(Continued)

(56) References Cited

U.S. PATENT DOCUMENTS 4,522,513 A  *  6/1985  Nozue ................... F16C 17/18
                                                    384/368
4,662,358 A     5/1987  Farrar et al.
(Continued)

FOREIGN PATENT DOCUMENTS

WO    2012078873    6/2012
WO    2014107424    7/2014

OTHER PUBLICATIONS

European Patent Office, International Search Report and Written Opinion in PCT Application Serial No. PCT/US14/049393, dated Oct. 31, 2014.
(Continued)

*Primary Examiner* — Erin M Piateski
(74) *Attorney, Agent, or Firm* — Christopher & Weisberg, P.A.

(57) ABSTRACT

An implantable blood pump includes an impeller rotatable about a rotational axis, having a body with a bottom surface at a downstream end and a central opening centered about the axis extending at least partially through the body from the bottom surface. A projecting element, e.g., a shaft, extends from below the bottom surface into or through the opening to support the impeller. The body can be configured to drive a primary downstream blood flow along an exterior of the body to beyond a peripheral edge of the bottom surface, and to provide a secondary downstream blood flow through the opening and along the bottom surface to beyond the peripheral edge, the secondary flow improving washing of a bearing surface.

14 Claims, 6 Drawing Sheets

Related U.S. Application Data continuation of application No. 14/590,485, filed on Jan. 6, 2015, now Pat. No. 9,717,832.

(52) U.S. Cl.
CPC ........ *A61M 1/1013* (2014.02); *A61M 1/1029* (2014.02); *A61M 1/122* (2014.02)

(58) Field of Classification Search
USPC .......................................................... 600/16
See application file for complete search history.

(56) References Cited

U.S. PATENT DOCUMENTS

| | | | |
|---|---|---|---|
| 4,688,998 | A | 8/1987 | Olsen et al. |
| 5,267,940 | A | 12/1993 | Moulder |
| 5,352,180 | A | 10/1994 | Candelon et al. |
| 5,676,162 | A | 10/1997 | Larson, Jr. et al. |
| 5,820,542 | A | 10/1998 | Dobak, III et al. |
| 5,888,242 | A | 3/1999 | Antaki et al. |
| 6,042,532 | A | 3/2000 | Freed et al. |
| 6,066,086 | A | 5/2000 | Antaki et al. |
| 6,116,862 | A | 9/2000 | Rau et al. |
| 6,176,848 | B1 | 1/2001 | Rau et al. |
| 6,387,323 | B1 | 5/2002 | Afzal et al. |
| 6,527,699 | B1 | 3/2003 | Goldowsky |
| 6,540,658 | B1 | 4/2003 | Fasciano et al. |
| 6,610,004 | B2 | 8/2003 | Viole et al. |
| 6,783,328 | B2 | 8/2004 | Lucke et al. |
| 6,991,595 | B2 | 1/2006 | Burke et al. |
| 7,591,777 | B2 | 9/2009 | LaRose |
| 7,645,225 | B2 | 1/2010 | Medvedev et al. |
| 7,742,821 | B1 | 6/2010 | Vamos et al. |
| 7,850,594 | B2 | 12/2010 | Sutton et al. |
| 7,862,501 | B2 | 1/2011 | Woodard |
| 7,963,905 | B2 | 6/2011 | Salmonsen et al. |
| 7,988,728 | B2 | 8/2011 | Ayre |
| 8,096,935 | B2 | 1/2012 | Sutton et al. |
| 8,226,712 | B1 | 7/2012 | Frazier et al. |
| 8,333,727 | B2 | 12/2012 | Farnan |
| 2001/0031210 | A1 | 10/2001 | Antaki et al. |
| 2003/0074144 | A1 | 4/2003 | Freed et al. |
| 2005/0071001 | A1 | 3/2005 | Jarvik |
| 2005/0215843 | A1 | 9/2005 | Medvedev |
| 2006/0074465 | A1 | 4/2006 | Webb |
| 2007/0276480 | A1 | 11/2007 | Tansley et al. |
| 2009/0138080 | A1 | 5/2009 | Siess et al. |
| 2009/0182188 | A1 | 7/2009 | Marseille et al. |
| 2009/0203957 | A1* | 8/2009 | LaRose ............ A61M 1/122 600/18 |
| 2010/0168848 | A1 | 7/2010 | Horvath et al. |
| 2011/0015693 | A1 | 1/2011 | Williamson |
| 2011/0144413 | A1* | 6/2011 | Foster ............ A61M 1/1017 600/16 |
| 2011/0238172 | A1* | 9/2011 | Akdis ............ F04D 13/0666 623/3.11 |
| 2012/0078030 | A1 | 3/2012 | Bourque |
| 2012/0150291 | A1 | 6/2012 | Aber et al. |
| 2012/0172657 | A1 | 7/2012 | Marseille et al. |
| 2014/0073837 | A1 | 3/2014 | Kerkhoffs et al. |

OTHER PUBLICATIONS

International Preliminary Report on Patentability for PCT Application No. PCT/US13/57986 dated Mar. 26, 2015.
International Search Report and Written Opinion for PCT Application No. PCT/US13/57986 dated Apr. 9, 2014.
U.S. Patent and Trademark Office, Invitation to Pay Additional Fees in PCT Application No. PCT/US13/57986, dated Jan. 23, 2014.

* cited by examiner

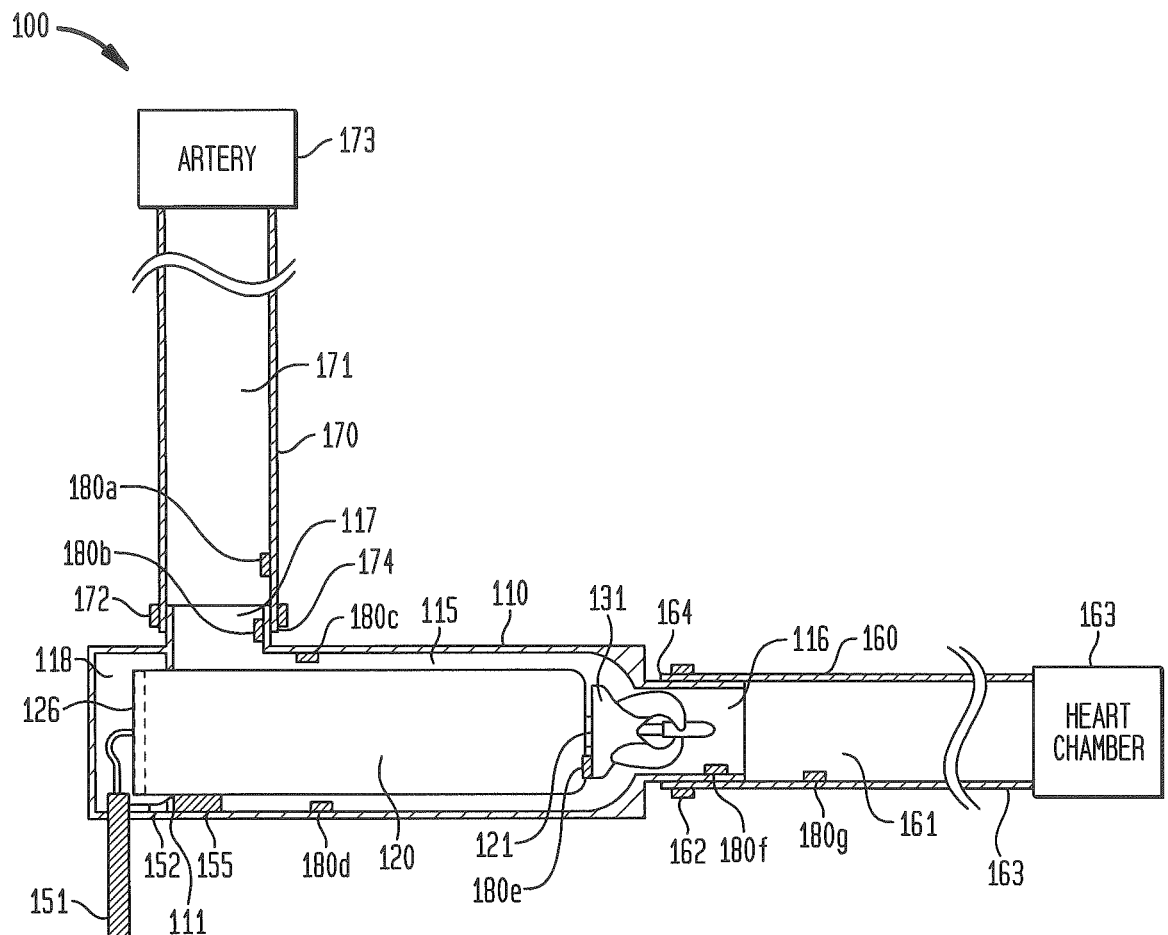
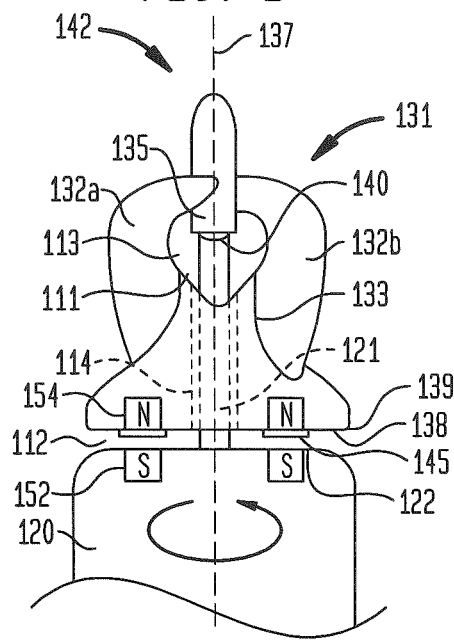
FIG. 1
FIG. 2

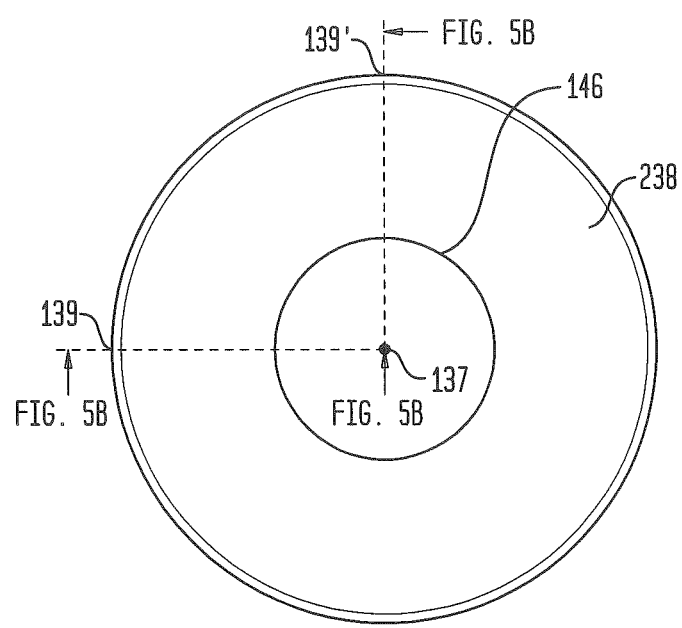
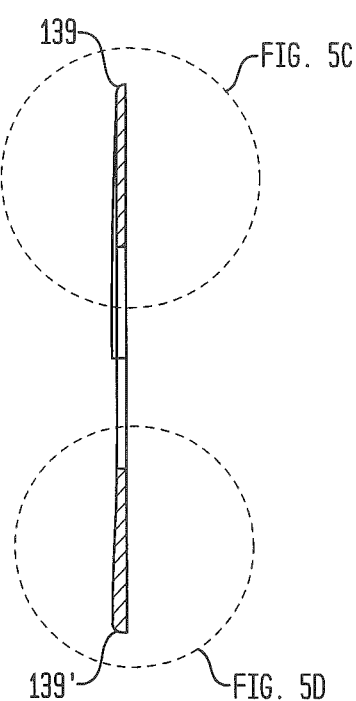
FIG. 5A FIG. 5B
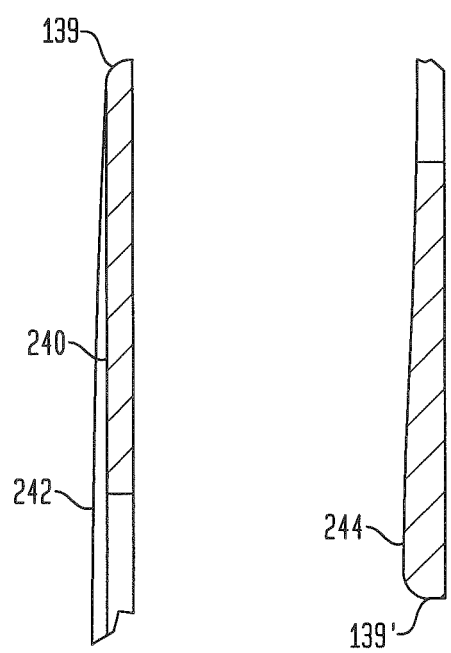
FIG. 5C  FIG. 5D  FIG. 5E

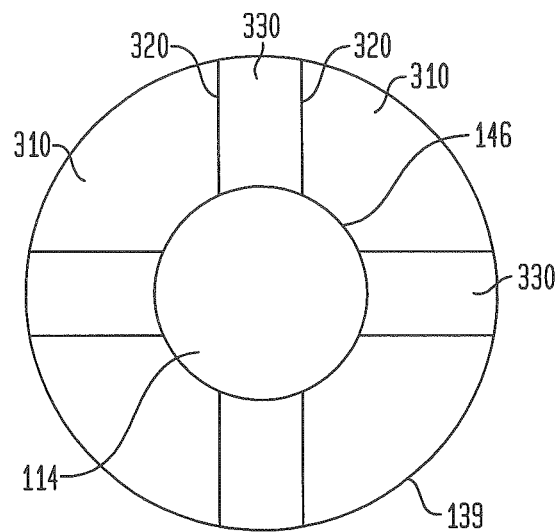
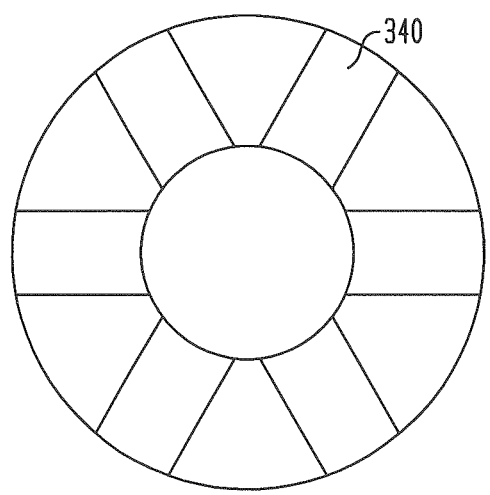

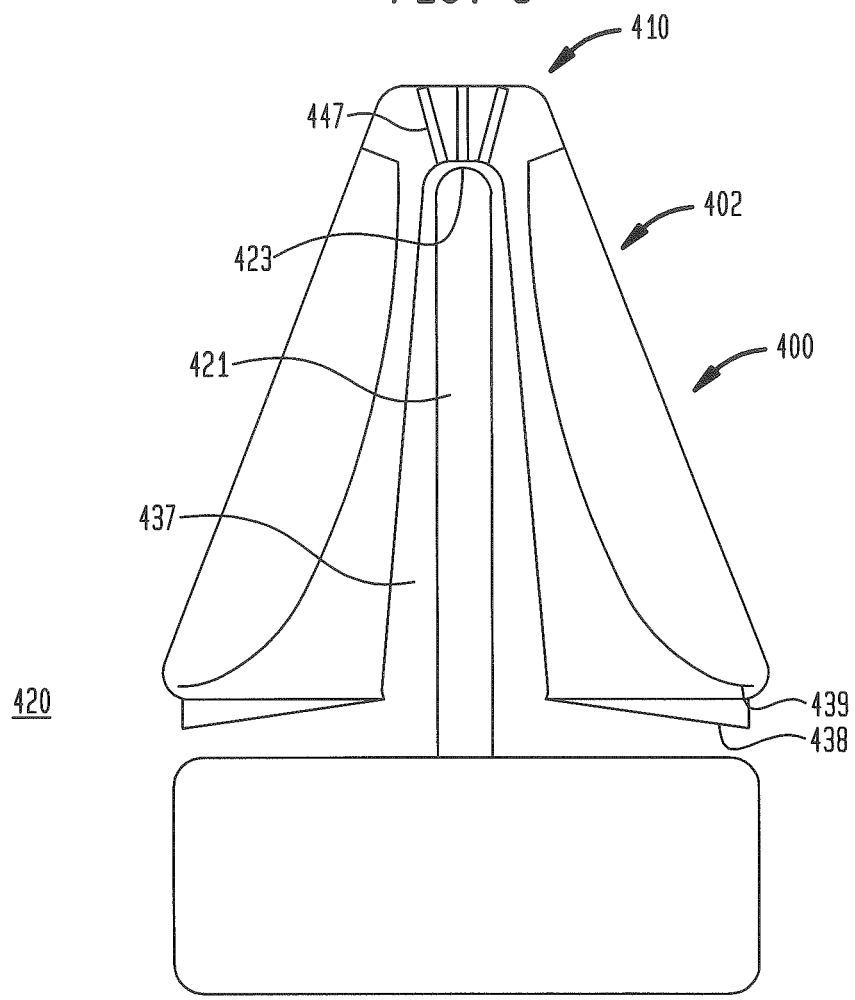

AXIAL FLOW ROTOR WITH DOWNSTREAM BEARING WASH FLOW

CROSS-REFERENCE TO RELATED APPLICATION

This application is a continuation of patent application Ser. No. 15/639,131, filed Jun. 30, 2017 and is a continuation of patent application Ser. No. 14/590,485, filed Jan. 6, 2015, entitled AXIAL FLOW ROTOR WITH DOWNSTREAM BEARING WASH FLOW, the entirety of which is incorporated herein by reference.

STATEMENT REGARDING FEDERALLY SPONSORED RESEARCH OR DEVELOPMENT n/a

TECHNICAL FIELD

The present invention relates to impellers for blood pumps.

BACKGROUND

Implantable pumps are used for a variety of medical purposes for pumping bodily fluids such as blood. For example, when the output of the heart is insufficient to meet the circulatory needs of a person or animal, a pump can be implanted to boost circulation.

The pump can be implanted within the human body to augment the blood flow from the left ventricle of the heart to the body in patients with diminished heart function, such pumps being referred to as left ventricular assist devices ("LVADs").

Referring to FIG. 1, a general description of a blood pump within a system for pumping blood can be as found in United States Pre-Grant Publication 2014/0073837 entitled "Blood Flow System with Variable Speed Control," the disclosure of which is incorporated by reference herein. System 100 includes a housing 110 surrounding a rotational drive assembly including motor 120 and fluid drive element 130 such as impeller 131. In some embodiments, system 100 comprises a rotational drive assembly similar to that described in U.S. Pat. No. 6,116,862 entitled "Blood Pump", or U.S. Pat. No. 6,176,848 entitled "Intravascular Blood Pump", the disclosures of said patents also being incorporated by reference herein. Impeller 131, is magnetically coupled with and rotated by a spinning drive mechanism 120 having a set of magnetic poles 152 coupled across gap 112 with corresponding magnetic poles 154 of the impeller 131 through force of magnetic attraction. Drive mechanism 120 includes a motor (not shown) which rotates poles 152 around the common axis 137 of the drive motor and impeller. A supporting element such as a shaft 121 extending through a central opening 114 can support the impeller while the impeller is rotating and held in place axially by the magnetic attraction from the drive mechanism 120. The pump chamber 115 includes the open space between a tubular portion of the housing 110 and other components of the pump such as impeller 131, shaft 121 and motor 120. In some embodiments, the chamber 115 comprises a volume less than 100 mL, for example less than 50 mL. In some embodiments, chamber 115 comprises a volume less than 10 mL, for example less than 5 mL, such as less than 2.5 mL or less than 1.2 mL.

Housing 110 comprises two ports, inlet port 116 and outlet port 117. When impeller 131 is rotated, fluid propulsion forces are generated such that fluid flows from inlet port 116 to outlet port 117 through chamber 115. A hollow tube, inlet cannula 160 includes proximal end 163, distal end 164 and lumen 161 therebetween. Inlet cannula 160 is attached and/or is attachable to inlet port 116 at its distal end 164, such as via a compression fitting 162. In some embodiments, proximal end 163 of inlet cannula 160 is configured to be fluidly attached to a source of blood, such as a source of oxygenated blood, such as at the left ventricle of a patient. In some embodiments, inlet cannula 160 can be configured as described in U.S. patent application Ser. No. 12/392,623, entitled "Devices, Methods and Systems for Establishing Supplemental Blood Flow in the Circulatory System", published as U.S. Pre-Grant Publication No. 2009/0182188, the disclosure of which is incorporated herein by reference.

A second hollow tube, outlet cannula 170 includes proximal end 173, distal end 174 and lumen 171 therebetween. Outlet cannula 170 is attached and/or is attachable to outlet port 117, such as via a compression fitting 172. In embodiments wherein inlet cannula 160 is attached to a source of arterial blood, distal end 174 of outlet cannula 170 can be configured to be fluidly attached to a blood vessel, such as an artery, such as via an anastomosis. In some embodiments, outlet cannula 170 can comprise an anastomotic connector on its distal end 174, such as is described in U.S. Pat. No. 8,333,727, entitled "Two Piece Endovascular Anastomotic Connector", the disclosure of which is incorporated herein by reference.

Housing 110, inlet cannula 160 and outlet cannula 170 are typically implanted in the patient, while other components such as control module 150 can be implanted in the patient, or can be coupled with motor 120 via a percutaneous cable 151. In some embodiments, impeller 131 and motor 120 are constructed and arranged to achieve a flow rate of blood of at least 0.3 L/min. In some embodiments, the system is configured to provide a flow rate of blood between 2.0 and 6.0 L/min. In some embodiments, the fluid flow system allows the speed to be set (e.g., automatically or manually) to a level between a minimum speed and a maximum speed. A typical speed of the impeller is several tens of thousands of revolutions per minute (rpm).

Areas of insufficient flow, such as low-flow areas within or proximate to the pump can result in circulated blood undesirably transitioning to solid matter. With blood pumping systems, blood in a stasis or near-stasis condition can transition to thrombus. Creation of a thrombus or other solid matter can result in reduced flow of blood through the pump or release of solid matter into the patient as an embolus.

For these and other reasons, there is a need for devices, systems and methods which reduce the potential for blood to stagnate and which may improve the washing of blood on a bearing surface of the pump, which can decrease the risk that blood will transition to solid matter.

SUMMARY

Provided herein are blood flow and other fluid flow systems, methods and devices for a human or animal, e.g., a mammal. A blood flow system can be implanted or partially implanted in a human or animal to circulate blood through the cardiovascular system. The systems, methods and devices of the present inventive concepts are constructed and arranged to continuously or intermittently eliminate points of flow stasis or other low-flow areas that may serve as stagnation points that could transition to thrombi and emboli. Systems disclosed herein include rotational drive assemblies, such as motors, and fluid drive elements such as impellers which are configured to pump bodily fluids such as blood.

An embodiment of the present invention provides an impeller, e.g., a rotor, for an implantable pump for pumping a fluid such as blood. The impeller is configured for driving a primary flow of the fluid along an exterior of the impeller to a region beyond a peripheral edge at a bottom surface of the impeller at a downstream end of the impeller. The impeller may comprise fluid driving surfaces such as blades or channels or the like. The fluid driving surfaces are configured to drive the primary flow in a downstream direction along the exterior of the impeller to a region beyond the peripheral edge of the impeller.

The impeller can be configured to drive a secondary flow of blood in a downstream direction through the central opening of the impeller and then outwardly along a bottom surface of the impeller such that the secondary flow then exits to the region beyond the peripheral edge of the bottom surface of the impeller. At the location beyond the impeller's peripheral edge, the secondary flow rejoins the primary flow and flows further downstream towards an outlet of the pump.

An implantable blood pump may include an impeller rotatable about a rotational axis, having a body with a bottom surface at a downstream end and a central opening extending through the body from an upstream entrance to the bottom surface and centered about the axis. A projecting element, e.g., a shaft extends from below the bottom surface into or through the opening to support the impeller. The body is configured to drive a primary blood flow along an exterior of the body to beyond a peripheral edge of the bottom surface, and to provide a secondary downstream flow through the opening, and then along the bottom surface to beyond the peripheral edge. The secondary downstream flow proximate to a bearing surface at an end of the projecting element may improve washing of the bearing surface.

In a particular embodiment, the impeller may comprise a hub aligned with the rotational axis and the central opening. In some embodiments, the hub is supported above a bearing surface which is spherical in form or otherwise in form of a surface of revolution about the axis. A projecting element, e.g., a shaft may extend from below the bottom surface at least partially through the opening and may have a socket configured to receive the bearing surface, such that the impeller is supported for rotation above the bearing surface atop the shaft, wherein the secondary downstream flow can improve washing of the bearing surface.

In accordance with an aspect of the invention, an impeller for a blood pump is provided. A body of the impeller may have a bottom surface at a downstream end of the body and a central opening extending at least partially through the body from the bottom surface, the central opening centered about a rotational axis of the body. The body can be configured to rotate about an element projecting from a surface below the bottom surface into the opening to drive a primary blood flow along an exterior of the body to beyond a peripheral edge of the bottom surface, and the body is configured to drive a secondary blood flow through the opening and along the bottom surface beyond the peripheral edge.

In accordance with one or more embodiments of the invention, the body may comprise a plurality of ridges protruding in an axial direction below portions of the bottom surface, the ridges defining a plurality of fluid channels for driving the secondary flow between the opening and the peripheral edge.

In accordance with one or more embodiments of the invention, the ridges may be blades elongated in a direction from the opening towards the peripheral edge. In some embodiments, the fluid channels may have arcuate shape. In some embodiments, the ridges may have straight walls defining the plurality of fluid channels. In some embodiments, the ridges may taper in a direction from the peripheral edge towards the opening. In some embodiments, the walls of each fluid channel may be parallel. In some embodiments, each fluid channel may extend in a radial direction from the opening to the peripheral edge.

In a particular embodiment, the bottom surface may undulate in a direction of a circumference of the bottom surface between each of a plurality of troughs and each of a plurality of respective elevations. In such embodiment, the troughs and elevations of the bottom surface may be configured to drive the secondary flow of the fluid towards the peripheral edge of the bottom surface.

In one or more embodiments, the impeller may include a bearing surface disposed within or adjacent the central opening. The bearing surface may be arranged to cooperate with a mating bearing surface to control position of the impeller in at least one direction.

In one or more embodiments, the bearing surface of the impeller may be disposed adjacent the upstream end of the central opening. In one or more embodiments, the impeller may be configured to drive the secondary flow to an area proximate the bearing surface to provide washing of the bearing surface.

In one or more embodiments, the central opening may extend through the body to an upstream entrance, and the impeller may include a hub aligned with the axis and the opening, the hub supporting the impeller atop the bearing surface.

In one or more embodiments, the impeller may comprise blades projecting from the exterior of the body for driving the primary flow.

In accordance with an aspect of the invention, an impeller for a blood pump is provided. The impeller may comprise an impeller body having a bottom surface at a downstream end of the body and a central opening extending at least partially through the body from the bottom surface. The central opening can be centered about a rotational axis of the body. The body can be configured to rotate about an element projecting from below the bottom surface into the opening to drive a primary downstream blood flow along an exterior of the body to beyond a peripheral edge of the bottom surface and axially downstream from the impeller, and the body can be configured to drive a secondary downstream blood flow through the opening and along the bottom surface to beyond the peripheral edge. The pump may be configured to rotate the body about the axis.

In accordance with one or more embodiments, a bearing surface may be provided for supporting rotation of the impeller body atop a shaft extending along the axis through the opening. The base may comprise a plurality of axially protruding ridges for driving the secondary downstream blood flow from the opening towards the peripheral edge, the ridges defining a plurality of fluid channels each disposed between a pair of the ridges. The ridges may be elongated in a direction from the opening towards the peripheral edge. In a particular embodiment, the fluid channels may have arcuate shape.

In one or more embodiments, the ridges may have straight walls defining the plurality of fluid channels. In one or more embodiments, the walls of each fluid channel are parallel. In one or more embodiments, each fluid channel may extend in a radial direction from the opening to the peripheral edge.

In one or more embodiments, the impeller may include a bearing surface disposed within or adjacent the central opening, said bearing surface being arranged to cooperate with a mating bearing surface to control position of the impeller in at least one direction.

In one or more embodiments, the central opening can extend through the body to an upstream entrance, and the impeller may include a hub aligned with the axis and the opening, the hub supporting the impeller atop the bearing surface.

In one or more embodiments, the impeller may comprise blades projecting from the exterior of the body for driving the primary flow.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 is a schematic illustration of a fluid flow system for pumping a liquid fluid, e.g., blood;

FIG. 2 is a detailed view of an impeller in accordance with an embodiment of the invention;

FIG. 5A is a plan view illustrating an alternative fan structure for driving a secondary flow of a fluid by an impeller in accordance with an embodiment of the invention;

FIGS. 5B, 5C and 5D each represent portions of a sectional view of the fan structure of FIG. 5A along portions of section lines A-B of FIG. 5A;

FIG. 5E illustrates a further sectional view of the fan structure of FIG. 5A in accordance with the embodiment seen in FIG. 5A;

FIG. 6 illustrates a plan view of a fan structure for an impeller in accordance with a variation of the embodiment seen in FIG. 3;

FIG. 7 illustrates a plan view of a fan structure for an impeller in accordance with another variation of the embodiment seen in FIG. 3; and FIG. 8 illustrates an elevation view of an alternative impeller in accordance with an embodiment of the invention.

DETAILED DESCRIPTION

Figure 2A:
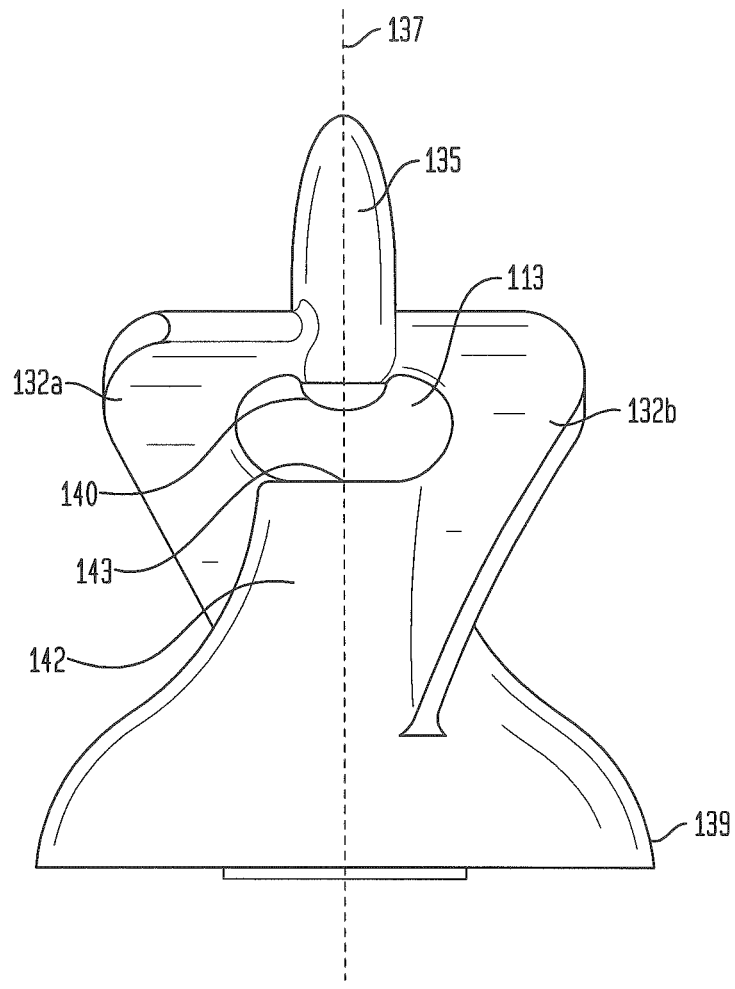
FIG. 2A is a detailed view of an impeller in accordance with a variation of the embodiment seen in FIG. 2.
Figure 3:
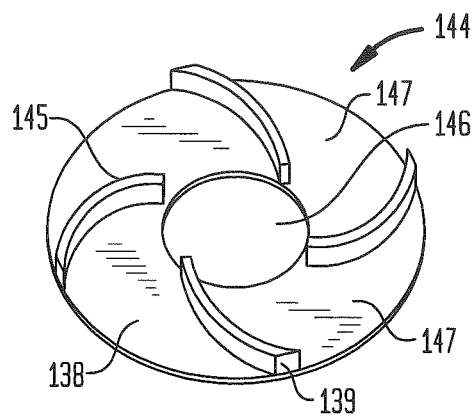
FIG. 3 is a perspective view illustrating a fan structure for driving a secondary flow of a fluid by an impeller in accordance with an embodiment of the invention.

FIGS. 2 and 3 depict an impeller 131 in accordance with an embodiment of the invention. As seen therein, the impeller 131 can comprise a body which tapers from a peripheral edge 139 at a bottom surface 138 of the body towards an upstream entrance 111 of a central opening 114 that is closer to an upstream end 142 of the impeller. The opening 114 is centered about a rotational axis 137 of the impeller and may extend entirely through the body between the upstream entrance 111 and the bottom surface 138 of the impeller.

As used herein, directions aligned with or parallel with an axis of rotation of the impeller is referred to as axial directions. More generally, the direction of the flow of blood between an inlet of the pump and an outlet of the pump is referred to as a "downstream" direction, and the direction opposite thereto is referred to as an "upstream" direction. In addition, a statement that an element is "downstream from" another means that such element is closer to the outlet of the pump than the other element; conversely, a statement that an element is "upstream from" another means that such element is closer to the inlet of the pump than the other.

Impeller 131 is configured to drive an axial flow of blood into a chamber disposed axially downstream of the impeller such as chamber 115 shown in FIG. 1. In a particular embodiment as seen in FIG. 2, the impeller may have a hub 135 configured to support the impeller atop a shaft 121, the hub being aligned with the axis of rotation 137 and the central opening 114. In some cases, the hub 135 may include a bearing surface for supporting the hub atop the shaft, or an element 140 having a bearing surface can be interposed between the hub and the shaft. Thus, in one embodiment, a bearing element 140 is in form of a spherical ball bearing and have a spherical surface. Shaft 121 extending through the central opening 114 may have a socket at an end thereof which is configured to receive a surface of the bearing element 140. While the pump is rotating, the ball bearing may spin as well, such that blood is drawn into the space between the socket and the ball bearing by the relative lower pressure created by the curved bearing surface. Alternatively, the bearing element 140 can be fixed to hub.

In other embodiments, the bearing surface may have a shape such as a surface of revolution about the rotational axis 137 of the impeller. In one example, the bearing surface may have a truncated spherical shape, or in other examples, a truncated spheroidal or ellipsoidal shape.

The impeller may have fluid driving surfaces such as blades, fluid channels, etc., for driving a primary flow of the fluid along the exterior of the impeller into a space beyond the peripheral edge of the base. For example, as seen in FIG. 2, the impeller may have two fluid propulsion blades, arms 132a and 132b, which extend from the hub 135 to connection points 133 at an exterior surface of the impeller 131 for driving a primary flow of the fluid, e.g., blood, along the exterior surface to a region beyond a peripheral edge 139 of the impeller such as the region of chamber 115 downstream of the impeller. Washout area 113 comprises an opening between the hub 135 and arms 132a and 132b as shown.

As further seen in FIG. 2, a gap 112 is provided between a bottom surface 138 at a base of the impeller 131 and a surface 122 juxtaposed therewith, such as a surface of a housing of an impeller drive mechanism 120 (FIG. 1). The impeller 131 can be configured to draw a secondary flow of the fluid from a region exterior to the impeller into washout area 113, then into the central opening 114 and then downstream along a surface of the shaft 121 within opening, and finally along the bottom surface 138 of the base outwardly through gap 112 into a region disposed beyond the peripheral edge 139. This downstream secondary flow adds to the overall downstream flow of the pump. The downstream secondary flow passing through the washout area 113 and downwardly into the opening 114 can improve washing of the bearing surface 140 provided between the shaft 121 and hub 135. In this way, lubrication can be improved at the junction between the bearing surface and the receiving socket. The downstream secondary flow may also aid in preventing stagnation of the blood, decreasing risk of thrombi or emboli.

In one example, the downstream secondary flow measured in units of fluid volume per time, may range between two percent and 30 percent of the primary flow driven by the impeller. In another example, the secondary flow rate may range between five and 25 percent of the primary flow rate. In yet another example, the secondary flow rate may range between 10 and 20 percent of the primary flow rate.

As further seen in FIG. 2, the impeller may have a unitary structure in which a body of the impeller can be constructed of a single monolithic piece of metal, which may include, inter alia, a ferro-magnetic or platinum cobalt alloy where arms 132a, 132b are shown connecting the hub 135 with integral portions of the base of the impeller. In one embodiment, the impeller 131 can be made entirely of a ferro-magnetic material and may have permanently magnetized areas therein which defines poles 154. In this case, the impeller may operate as a rotor driven by a rotating magnetic field produced by motor 120. Alternatively, the impeller can be constructed of a combination of metals and elements such as magnets which can be embedded in the structure. In one example, arms 132a, 132b can be attached by welding, brazing, or other appropriate attachment technique. As seen in FIG. 2, the hub 135 and bearing surface 140 can be displaced upwardly away from an entrance 111 to central opening 114 in a direction of the axis 137 to provide easy entry to washout area 113. Entrance 111 to the opening defines a nonplanar arcuate edge of the body. For example, the entrance 111 to the opening is heart-shaped in cross-section. As further seen in FIG. 2, the entrance 111 to the opening may define troughs between the arms 132a and 132b of the impeller which extend downwardly towards the downstream end of the impeller. In addition, the entrance 111 may extend upstream and define an edge which extends in a direction of an edge of the arm 132a or 132b adjacent thereto.

Alternatively, in the example impeller shown in FIG. 2A, the entrance 143 to the opening in the body may have a circular edge which is disposed in a plane orthogonal to the axis 137.

A variety of structures, surfaces and shapes of surfaces can be provided in order for impeller to drive the downstream secondary flow through washout area 113, through the entrance 111 of central opening 114, and outwardly through gap 112 beyond the peripheral edge 139 at a downstream end of the impeller. Thus, as further seen in FIGS. 2 and 3, a fan structure 144 can be disposed at a bottom surface 138 at the downstream end of the impeller. The fan structure includes a plurality of ridges 145 projecting in a direction parallel to axis 137 from other portions of the bottom surface. Thus, the ridges 145 define a plurality of fluid channels 147 between them for driving the secondary flow through the washout area, through the central opening and outwardly through gap 112. In one embodiment, the fan structure 144 at the bottom surface 138 can be formed integrally with the body of the impeller. Alternatively, the fan structure can be formed separately and then fused to the impeller such as by welding, biocompatible adhesive, or attached using fasteners or any other biocompatible attachment technique. As used herein, "bottom surface" shall mean a surface at a downstream end of the impeller which faces away from the body of the impeller. As assembled in the pump, the bottom surface 138 can be juxtaposed with a surface, such as surface 122 of the impeller drive mechanism 120.

In one example, as seen in FIG. 3, the ridges 145 are blades at the bottom surface which are elongated in a direction extending from the exit 146 of the central opening towards the peripheral edge 139 of the impeller. In the example seen in FIG. 3, the blades 145 and fluid channels between the blades have arcuate shape. The fan structure may have four ridges 145 as blades on the bottom surface 138 of the impeller as shown in FIG. 3, or there can be a greater number or fewer number of ridges 145.

Figure 4A:
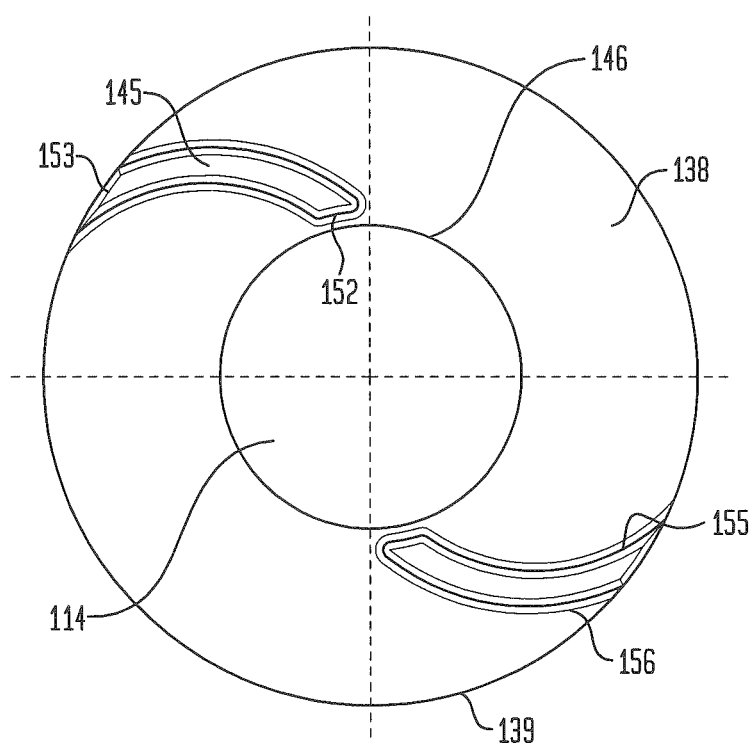
FIG. 4A is a plan view illustrating a fan structure for driving a secondary flow of a fluid by an impeller in accordance with an embodiment of the invention.
Figure 4B:
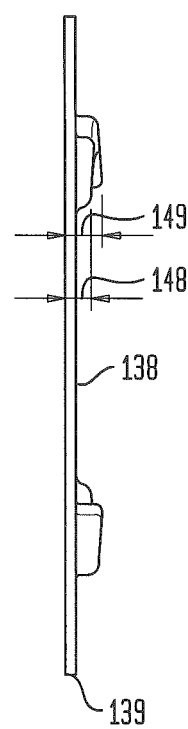
FIG. 4B is a corresponding sectional view of the fan structure seen in FIG. 4A.

In a further example shown in FIGS. 4A and 4B, the fan structure may have only two arcuate ridges 145 or blades, each ridge extending from locations proximate the exit 146 of the opening towards, that is, up to or adjacent to the peripheral edge 139 of the impeller base. FIG. 4B represents a projection of the ridges 145 or blades in a vertical direction parallel to axis 137 above the bottom surface 139 of the impeller base. In one example, a height of each blade may decrease with distance along each blade away from the opening 114. In such case, each blade may have a greater height 149 near an end 152 of such blade proximate to the opening 114 than its height 148 nearer to or closest to the peripheral edge 139. As further seen in FIG. 4A, junctions between the edges 155, 156 of the blades and the bottom surface 138 can be radiused. Alternatively, in some cases the junctions may not be radiused. The blade edge to bottom surface junction radius can be the same on each edge 155, 156 of each blade or can be different depending on whether the edge of the blade curves inward upon itself as seen in the case of edge 155, or whether the edge of the blade curves outward as seen for edge 156.

In a variation of the embodiment illustrated in FIGS. 4A and 4B, a height of each blade may increase with distance from the opening 114 such that each blade has a greater height near the end 153 proximate to the peripheral edge 139 than the height of such blade at or near the end 152 closest to the opening 114.

FIGS. 5A through 5E illustrate contours of a bottom surface 238 of an impeller in accordance with another embodiment of the invention. In this case, the bottom surface 238 can be formed with a shape that undulates up and down in a circumferential direction about the rotational axis 137. In this case, the fluid flows from the exit 146 of the central opening onto the bottom surface 238 where it then flows into lower spaces, e.g., troughs in the undulating bottom surface 238 which lie between the higher elevations or crests of the bottom surface. The higher elevations of the bottom surface help to confine and move the fluid along the bottom surface to the region beyond the peripheral edge 139 of the impeller base. In effect, the elevations or crests of the undulating surface serve as ridges to impel the flow, whereas the troughs act as flow channels.

FIG. 5B illustrates elevational views of the bottom surface 238 along sections A-A and A-B shown in FIG. 5A. FIG. 5C is an elevational view illustrating a height of the bottom surface along the section line A-A extending from a point on peripheral edge 139 towards the rotational axis 137 of the impeller. As seen in FIG. 5C a portion 240 of the bottom surface extending along line A-A is at a lower height than a height of another portion 242 of the bottom surface that is at a different circumferential position on the bottom surface. On the other hand, as seen in FIG. 5D, a portion 244 of the bottom surface extending along section line A-B between axis 137 and a point 139' at the peripheral edge lies at a greater height than other portions of the bottom surface such as portion 240, for example. FIG. 5E illustrates a further example in which peak height of the bottom surface is reached near the center of the bottom surface, and may decrease in height with proximity to the peripheral edge.

In accordance with another embodiment as seen in FIG. 6, a plurality of ridges 310 in the bottom surface have straight walls 320 which define a plurality of fluid channels 330 extending away from the downstream exit 146 of the opening towards the peripheral edge 139 of the bottom surface. Four fluid channels 330 can be provided for channeling the fluid along the bottom surface from the opening 114 to locations beyond the peripheral edge 139. As seen in FIG. 6, the walls 320 of each fluid channel 330 can be parallel, and each fluid channel extends in a radial direction from the opening 114 to the peripheral edge 139. In one example seen in FIG. 6, the ridges 310 taper inwardly from the peripheral edge 139 towards the opening 114.

FIG. 7 illustrates a variation of the embodiment seen in FIG. 6 which provides six fluid channels 340 instead of four fluid channels 330. Other characteristics and features of the bottom surface can be the same as seen in FIG. 6.

As seen in FIG. 8, in a variation of the above-described embodiments, the body 400 of an alternative impeller is of unitary construction, with fluid-driving surfaces or channels 402 arranged between an upstream end 410 of the impeller and a downstream end 420. In a particular embodiment, the shape of the impeller can be generally conical, tapering from the downstream end 420 towards the upstream end 410. In such embodiment, the central opening 437 may not extend entirely through the impeller body 400, but instead be configured as a cavity into which a supporting element such as a shaft 421 may project. One or more through openings 447 may extend through a portion of the impeller and connect with the central opening 437 to permit blood to flow from outside the upstream end 410 of the impeller into the central opening 437. Similar to the above-described embodiments, fluid driving elements such as the ridges or blades at the bottom surface drive the blood through the at least one opening 447 into the central opening 437 and then outwardly along the bottom surface 438 to a region beyond the peripheral edge 439 of the bottom surface.

As further seen in FIG. 8, the impeller can be configured to spin atop a thin film of blood which flows past an extremity 423 of the supporting element 421, wherein the extremity of the supporting element and the adjacent interior surface of the impeller serve as a bearing of the system. In a variation of the FIG. 8 embodiment, the supporting element can be provided with an additional bearing surface such as a ball bearing or other surface of revolution at the extremity 423, such bearing surface configured to provide additional wear resistance during operation. In still other embodiments, the bearing may include portions of the impeller within or near the central opening but near the downstream end of the impeller. For example, the surface of central opening 437 adjacent the bottom surface 438 can be configured as a bearing surface, and the central shaft 421 may have a mating bearing surface near its downstream end. In yet another embodiment, the bearing surfaces can be arranged to control the position of the impeller in directions transverse to the axis, in lieu of or in addition to the axial directions. For example, the central opening 437 can be arranged to form a sleeve bearing and the shaft 421 may form a journal for such a bearing. For example, such an arrangement can be used where other bearings control the axial position of the impeller. Also, the bearing surfaces can be arranged for physical contact lubricated by a film of blood, or else can be arranged as hydrodynamic bearing surfaces, where hydrodynamic action maintains a film of blood between the bearing surfaces and the forces acting between the surfaces can be transmitted between the surfaces though the film.

Although the invention herein has been described with reference to particular embodiments, it is to be understood that these embodiments are merely illustrative of the principles and applications of the present invention. It is therefore to be understood that numerous modifications can be made to the illustrative embodiments and that other arrangements can be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments can be shared with others of the described embodiments.

What is claimed is:

1. An impeller for a blood pump, comprising:
a ferromagnetic body having a bottom surface at a downstream end of the body and a central opening extending at least partially through the body from the bottom surface, the central opening centered about a rotational axis of the body, the rotational axis defining an axial direction; and
the body configured to rotate about an element projecting from a surface below the bottom surface into the central opening to drive a primary blood flow along an exterior of the body to beyond a peripheral edge of the bottom surface, and the body configured to drive a secondary blood flow through the central opening toward the bottom surface and then outwardly along the bottom surface to beyond the peripheral edge, the body including a bearing proximate a distal end of the element, the bottom surface undulates in a direction of a circumference of the bottom surface between troughs and respective elevations, the troughs and elevations of the bottom surface are configured to drive the secondary flow of the fluid towards the peripheral edge of the bottom surface.

2. The impeller of claim 1, wherein the undulations of the body define a plurality of ridges protruding in an axial direction below portions of the bottom surface, the ridges defining a plurality of fluid channels for driving the secondary flow between the opening and the peripheral edge.

3. The impeller of claim 2, wherein the ridges are blades elongated in a direction from the opening towards the peripheral edge.

4. The impeller of claim 3, wherein the fluid channels have arcuate shape.

5. The impeller of claim 3, wherein the ridges have straight walls defining the plurality of fluid channels.

6. The impeller of claim 5, wherein the ridges taper in a direction from the peripheral edge towards the opening.

7. The impeller of claim 6, wherein the walls of each fluid channel are parallel.

8. The impeller of claim 7, wherein each fluid channel extends in a radial direction from the opening to the peripheral edge.

9. The impeller of claim 1, wherein the impeller includes blades projecting from the exterior of the body for driving the primary flow.

10. An implantable blood pump, comprising:
a ferromagnetic impeller body having a bottom surface at a downstream end of the body and a central opening extending at least partially through the body from the bottom surface, the central opening centered about a rotational axis of the body, the rotational axis defining an axial direction;

the body being configured to rotate about an element projecting from below the bottom surface into the central opening to drive a primary downstream blood flow along an exterior of the body to beyond a peripheral edge of the bottom surface and axially downstream from the impeller, the body including a bearing proximate a distal end of the element; the body configured to drive a secondary downstream blood flow through the central opening toward the bottom surface and then outwardly along the bottom surface to beyond the peripheral edge, the bottom surface include a plurality of axially protruding ridges defining at least one fluid channel, the plurality of axially protruding ridges being configured to drive the secondary downstream blood flow from the opening towards the peripheral edge; and the pump being configured to rotate the body about the axis and to drive the blood in a generally axial direction downstream from the impeller.

11. The pump of claim 10, wherein each one of the plurality of axially protruding ridges is a blade elongated in a direction from the opening towards the peripheral edge, and the plurality of fluid channels have an arcuate shape.

12. The pump of claim 10, wherein each one of the plurality of axially protruding ridge has straight walls defining the at least one fluid channel, the straight walls extending in a radial direction from the opening to the peripheral edge.

13. The pump of claim 10, wherein the impeller comprises blades projecting from the exterior of the body for driving the primary flow.

14. The pump of claim 10, wherein the body comprises a plurality of magnetic poles proximate the bottom surface, the body being configured to be rotationally driven by and the axial position of the body being secured by an external rotating magnetic field.

* * * * *